(12) United States Patent
Govari et al.

(10) Patent No.: US 8,078,286 B2
(45) Date of Patent: Dec. 13, 2011

(54) TECHNIQUES FOR MINIMIZING RADIOFREQUENCY-INDUCED TISSUE HEATING

(75) Inventors: Assaf Govari, Haifa (IL); Andres Claudio Aitmann, Haifa (IL)

(73) Assignee: Biosense Webster, Inc., Diamond Bar, CA (US)

(*) Notice: Subject to any disclaimer, the term of this patent is extended or adjusted under 35 U.S.C. 154(b) by 208 days.

(21) Appl. No.: 11/565,261

(22) Filed: Nov. 30, 2006

(65) Prior Publication Data

US 2008/0132975 A1    Jun. 5, 2008

(51) Int. Cl.
*A61N 1/00* (2006.01)

(52) U.S. Cl. .......................................... 607/61

(58) Field of Classification Search ............. 607/33, 607/61
See application file for complete search history.

(56) References Cited

U.S. PATENT DOCUMENTS

| | | | | |
|---|---|---|---|---|
| 3,566,234 A | * | 2/1971 | Thomson | 455/19 |
| 4,193,405 A | * | 3/1980 | Abels | 604/362 |
| 4,314,373 A | * | 2/1982 | Sellers | 455/73 |
| 4,361,153 A | * | 11/1982 | Slocum et al. | 607/32 |
| 5,258,766 A | | 11/1993 | Murdoch | |
| 6,694,184 B2 | * | 2/2004 | Cappa et al. | 607/2 |
| 2002/0107445 A1 | * | 8/2002 | Govari | 600/437 |
| 2003/0023161 A1 | * | 1/2003 | Govari et al. | 600/423 |
| 2003/0120150 A1 | * | 6/2003 | Govari | 600/424 |
| 2005/0010203 A1 | * | 1/2005 | Edwards et al. | 606/32 |
| 2005/0027192 A1 | * | 2/2005 | Govari et al. | 600/424 |
| 2005/0099290 A1 | | 5/2005 | Govari | |

FOREIGN PATENT DOCUMENTS

| | | |
|---|---|---|
| CN | 1165458 | 11/1997 |
| CN | 1466301 | 1/2004 |
| EP | 0776176 B1 | 6/1997 |
| EP | 0 948 221 A2 | 10/1999 |
| JP | 8-251653 | 9/1996 |
| WO | 94/01941 | 1/1994 |
| WO | 97/08854 | 3/1997 |

OTHER PUBLICATIONS

Electromagnetic Fields (Environmental Health Criteria 137, 1992) http://www.inchem.org/documents/ehc/ehc/ehc173.htm.

* cited by examiner

*Primary Examiner* — Mark W Bockelman
*Assistant Examiner* — Roland Dinga
(74) *Attorney, Agent, or Firm* — Louis J. Capezzuto

(57) ABSTRACT

Methods and systems are provided for wirelessly powering a medical device in a living subject using external radiofrequency energy. A radiofrequency driving unit outside the subject irradiates the medical device. A passive antenna is positioned outside the subject, generally opposing the driving unit to redirect the field generally toward the device. The reradiating element increases uniformity of the electromagnetic field produced by the driving unit, which reduces local tissue heating in the subject and in personnel attending the subject.

19 Claims, 3 Drawing Sheets

TECHNIQUES FOR MINIMIZING RADIOFREQUENCY-INDUCED TISSUE HEATING

BACKGROUND OF THE INVENTION

1. Field of the Invention

This invention relates to remotely powering wireless devices. More particularly, this invention relates to minimizing heating of body tissues during exposure to an electromagnetic field while powering a wireless medical device.

2. Description of the Related Art

Implantable or insertable medical devices are sometimes wirelessly powered by the transmission of radiofrequency (RF) energy from a radiator that is located external to a patient's body. One or more power coils incorporated in the device receive the radiofrequency energy. For example, some wireless location transponders comprise such power coils, and one or more position sensing coils for receiving externally generated position signals. The transponders typically use the wirelessly received energy to convert the position signals into high frequency signals, and to drive the power coil (or a separate transmission coil) to transmit the high frequency signals to an externally located processing unit, which responsively determines the position and the orientation of the transponder.

For example, a transponder and apparatus for operating the transponder employing analog high-frequency signals is described in U.S. Patent Application Publication No. 2003/0120150, entitled "Wireless Position Sensor," whose disclosure is herein incorporated by reference. The apparatus for operating the transponder includes a plurality of field generators, which generate electromagnetic fields at different respective frequencies in a vicinity of the object, and a radiofrequency driver, which radiates a radiofrequency driving field toward a wireless transponder. The transponder includes at least one sensor coil, in which a signal current flows responsively to the electromagnetic fields, and a power coil, which receives the radiofrequency driving field and conveys electrical energy from the driving field to power the transponder. The power coil also transmits an output signal for communicating information to a receiver or interrogator. In medical applications such transponders, whether analog or digital, typically comprise multiple sensor coils, such as three mutually-orthogonal coils, as described in European Patent EP 0 776 176 to Ben-Haim et al. Position and orientation coordinates of the transponder can thus be determined without ambiguity.

These location transponders enable the determination of the position and orientation of an object in the body without the need for any wired connection between the sensing coil and the external processing unit. Such wireless transponders may be implanted in the body of a patient, such as in a bone of the patient, or incorporated into an implantable medical device. However, there is a concern that when the device is being actively powered by a radiofrequency driver, there could be harmful local tissue heating resulting from non-uniformities in the electromagnetic field.

In general the deposition of radiofrequency energy in the human body tends to increase the body temperature. A World Health Organization document, *Environmental Health Criteria* 137, available on the Internet at the URL "http://www.inchem.org/documents/ehc/ehc/ehc137.htm", indicates that there exists a threshold specific absorption rate (SAR) of radiofrequency energy for frequencies above about 1 MHz of 1-4 W/kg, above which there is increasing likelihood of adverse health effects. Below about one MHz, standards are based on induced currents in the body, causing shocks and burns. Furthermore, pulsed fields may be of particular concern. In the case of pulsed electromagnetic fields, it has been shown, under a number of conditions, that the thresholds for biological effects at frequencies above several hundred MHz are decreased when the energy is delivered in short (1-10 µs) pulses. A safe limit for such pulses cannot even be identified on the basis of available evidence. It would appear to be prudent to minimize exposure of patients and medical personnel to such fields.

SUMMARY OF THE INVENTION

According to disclosed embodiments of the invention, methods and systems are provided for wirelessly powering a medical device in a living subject using external radiofrequency energy while minimizing the local deposition of radiofrequency energy in tissues. A radiofrequency driving unit outside the subject irradiates the medical device. A passive antenna is positioned outside the subject, generally opposing the driving unit, which redirects the field generally toward the device. The reradiating element increases uniformity of the electromagnetic field produced by the driving unit, and thereby reduces local tissue heating in the subject and in personnel attending the subject.

An embodiment of the invention provides a method for wirelessly powering a medical device that is located in a living subject, which is carried out by generating a radiofrequency energy field at a first position outside the subject, the field extending into the subject to energize the device, and passively reradiating the field from a second position outside the subject generally toward the first position.

According to an aspect of the method, the second position generally opposes the first position across the subject.

According to another aspect of the method, the device is a transponder having position sensors that obtain power from the field.

In one aspect of the method, the field is reradiated by exactly one passive antenna at the second position.

According to a further aspect of the method, the passive antenna includes a single coil of wire.

According to yet another aspect of the method, the field has a frequency of 13.6 MHz and the passive antenna has a capacitance of about 100 pF.

In an additional aspect of the method, the field is resonated at the second position.

One aspect of the method includes shielding a portion of the subject from the field, the shielded portion excluding the device.

An embodiment of the invention provides an apparatus for wirelessly powering a medical device. The device is located in a living subject and is energized by external radiofrequency energy. A radiofrequency driving unit disposed at a first position outside the subject for generates a radiofrequency energy field that extends into the subject to irradiate the device. A reradiating element is disposed in the field at a second position outside the subject to redirect the field generally toward the device.

According to an additional aspect of the apparatus, the device is a transponder having position sensors that derive power from the field.

According to still another aspect of the apparatus, the reradiating element is exactly one passive antenna.

According to aspect of the apparatus, the passive antenna includes a single coil of wire.

According to a further aspect of the apparatus, the passive antenna is resonant at a frequency of the field.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, and control logic have not been shown in detail in order not to obscure the present invention unnecessarily.

Figure 1:
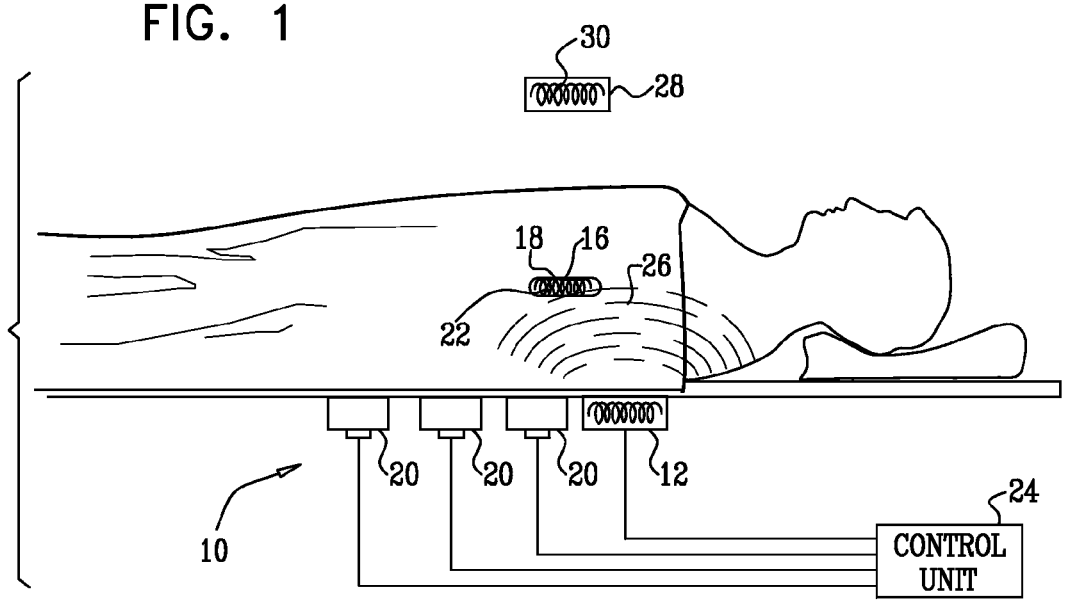
FIG. 1 is a pictorial illustration of a system for wirelessly energizing a medical device in accordance with a disclosed embodiment of the invention.

Turning now to the drawings, reference is initially made to FIG. 1, which is a pictorial illustration of a system 10 for wirelessly energizing a medical device in accordance with a disclosed embodiment of the invention. The system 10 comprises a power-driving unit 12 disposed external to a subject 14 and an implantable or insertable wireless medical device 16. The medical device 16 is typically incorporated in a catheter (not shown) or implanted in the subject 14. The medical device 16 comprises at least one power coil 18, for receiving energy transmitted by the power-driving unit 12. For applications in which the medical device 16 functions as a wireless location transponder, the system 10 typically further comprises one or more position signal generators 20, which generate position signals received by at least one position sensing coil 22 incorporated in the medical device 16. A control unit 24 controls and energizes the position signal generators 20 and the power driving unit 12.

A transponder, which is suitable for use as the medical device 16, and which transmits digital high-frequency signals is described in U.S. Patent Application Publication No. 2005/0099290 entitled, "Digital Wireless Position Sensor," whose disclosure is herein incorporated by reference.

In order to efficiently transmit power to the medical device 16, the power driving unit 12 is typically located near or in contact with external tissue of the subject 14, in a vicinity of the medical device 16. The power-driving unit 12 generates a radiofrequency signal, typically having a frequency in the megahertz range (e.g., 13.6 MHz), to drive the power coil 18 and thereby power the medical device 16. The strength of a RF field 26 generated by the power driving unit 12 typically drops off rapidly as the distance from the power driving unit 12 increases. Therefore, a relatively high power level (e.g., between about 12 W/kg and about 20 W/kg) is typically necessary in order to provide sufficient field strength at the medical device 16, which is typically positioned several centimeters to several tens of centimeters from the power driving unit 12, depending on the specific application. Such a strong field may undesirably heat tissue of the subject 14 in the vicinity of the power-driving unit 12, and tissues of the physician performing the procedure and ancillary medical personnel (not shown).

In order to increase the uniformity of the field 26, the system 10 further comprises a passive antenna 28, which typically comprises at least one coil or loop 30. For example, the antenna 28 may comprise a single 80 cm loop typically with about 100 pF capacitance. However, the capacitance may vary, so long as the loop is configured so as to resonate at the frequency of the field developed by the power-driving unit 12. The antenna 28 is positioned on the side of the subject 14 opposite the side on which the power-driving unit 12 is positioned, typically between about 1 and about 1.5 meters from the power-driving unit 12. The antenna 28 is typically entirely passive; it thus does not require a power source or coupling to a control unit. The antenna 28 re-radiates a portion of the field's energy. As a result, the field 26 is generally relatively stronger in the vicinity of the antenna 28 and of the medical device 16, and relatively weaker in the vicinity of the power-driving unit 12, than would be the case in the absence of the antenna 28.

Figure 2:
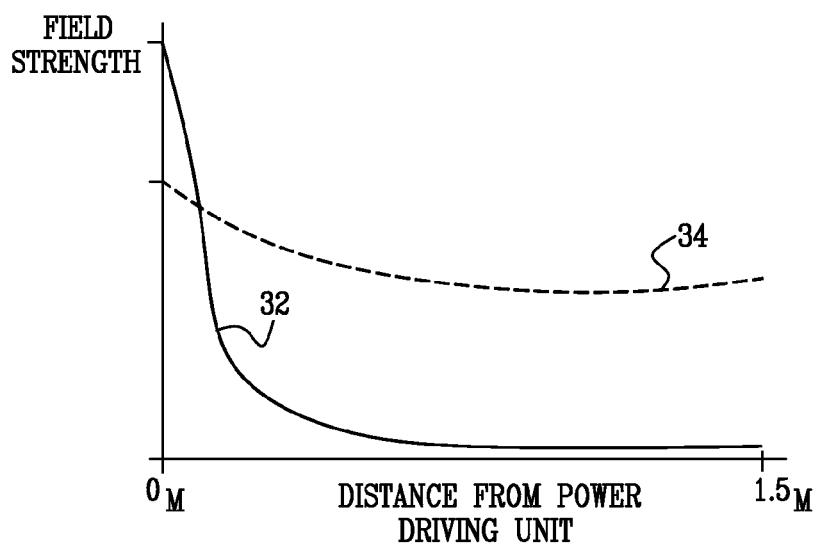
FIG. 2 shows exemplary field strength curves produced by the system shown in FIG. 1, in accordance with a disclosed embodiment of the invention.

Reference is now made to FIG. 2, which is a graph showing theoretical exemplary field strength curves, in accordance with a disclosed embodiment of the invention. In the theoretical example illustrated, a curve 32 represents the strength of the field 26 (FIG. 1), when the antenna 28 is not employed, at distances between 0 m and 1.5 m from the power-driving unit 12, in a generally upward direction from the power-driving unit 12 and through the subject 14. As can be seen, the strength drops off rapidly as the distance from the driving unit increases. A curve 34 represents the strength of the field 26, when the antenna 28 is deployed at 1.5 m from the power-driving unit 12. The re-radiation from the antenna 28 substantially flattens the curve, resulting in a more uniform field distribution.

Example

Figure 3:
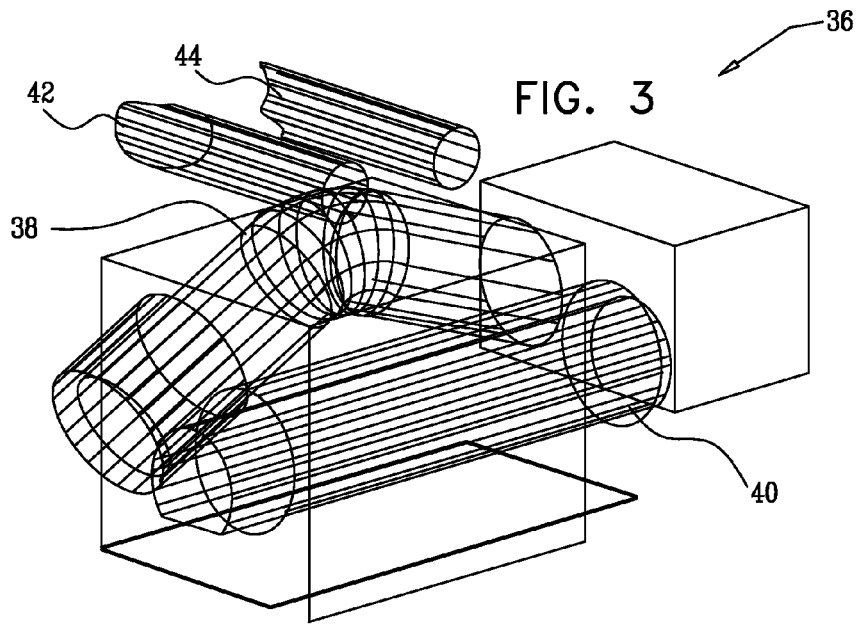
FIG. 3 is a finite element model of a human knee shown in slight perspective on an operating table, in which antennae are shown, in accordance with a disclosed embodiment of the invention.

Reference is now made to FIG. 3, which is a finite element model 36 of a human knee 38 shown in slight perspective on an operating table, in accordance with a disclosed embodiment of the invention. Muscle conductivity of 0.6 Seim was assumed for the models in this Example. A power-driving element 40 is disposed beneath the knee 38. Passive re-radiating antennae 42, 44 are situated above the knee 38.

Figure 4:
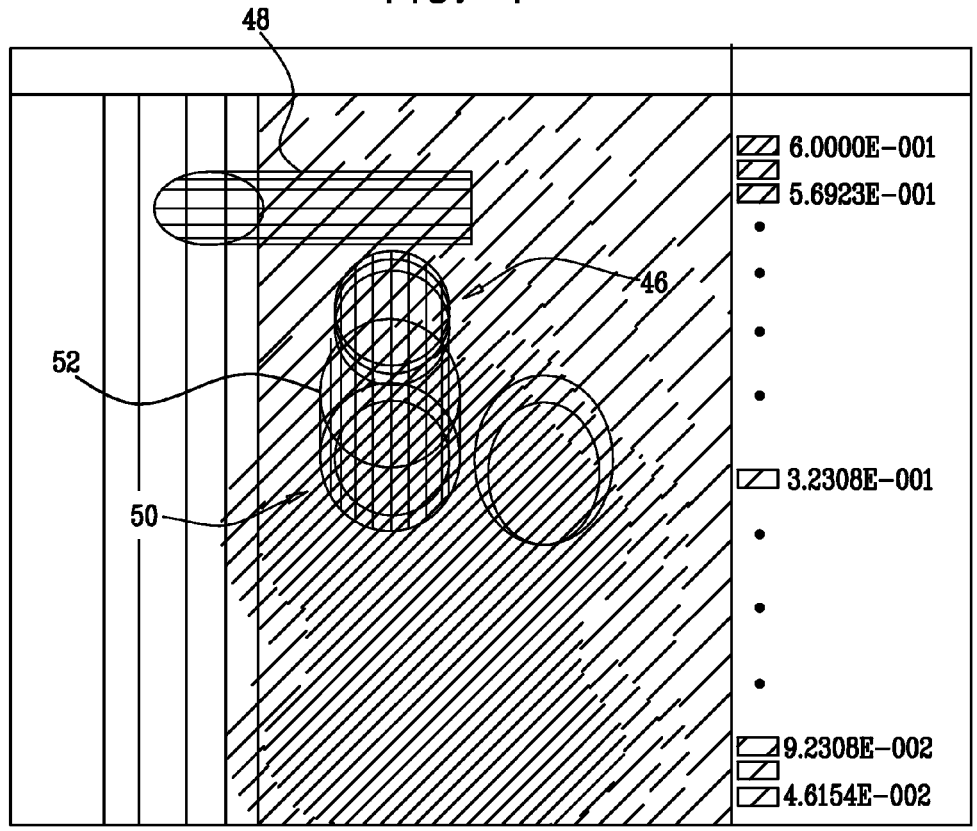
FIG. 4 is an end view of a finite element model similar to the finite element model shown in FIG. 3, over which a radiation pattern is superimposed, in accordance with a disclosed embodiment of the invention.

Reference is now made to FIG. 4, which is an end view of a finite element model 46 in accordance with a disclosed embodiment of the invention, similar to the finite element model 36 (FIG. 3), in which the antennae 42, 44 are absent. A simulated radiation pattern created by a driving element 48 is shown. An area 50 of intense RF radiation is indicated, overlapping an operative site 52.

Figure 5:
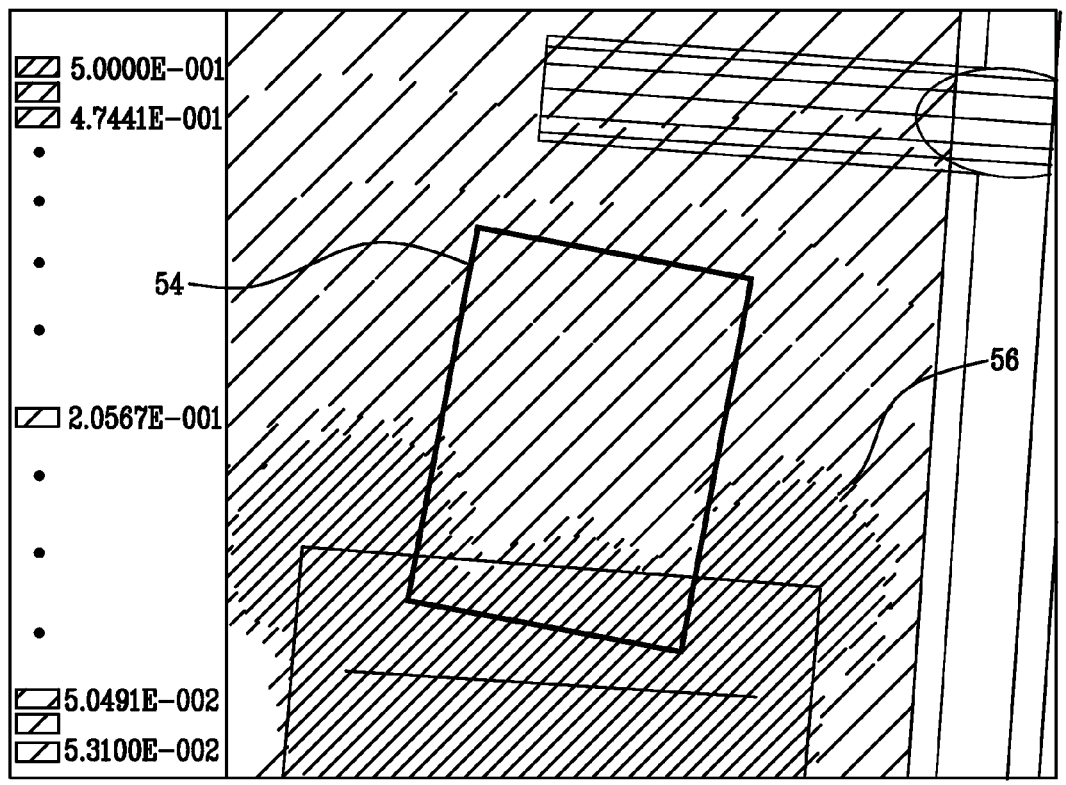
FIG. 5 shows a finite element model similar to FIG. 4 with a superimposed radiation pattern, in which antennae are active, in accordance with a disclosed embodiment of the invention.

Reference is now made to FIG. 5, which is a view of the finite element model 46, in which the antennae 42, 44 (FIG. 3) are now active in a simulation, in accordance with a disclosed embodiment of the invention. The perspective of FIG. 5 differs somewhat from FIG. 4, and most of the finite element model has been removed to better illustrate the radiation pattern. Instead, a rectangle 54 outlines the location of the knee component of the finite element model 46. The region of most intense RF radiation is indicated by an area 56, which is considerably reduced in size when compared to the area 50 (FIG. 4). Only a relatively small portion of the operative site in the lower portion of the rectangle 54 is occupied by the area 56.

Alternate Embodiment

Figure 6:
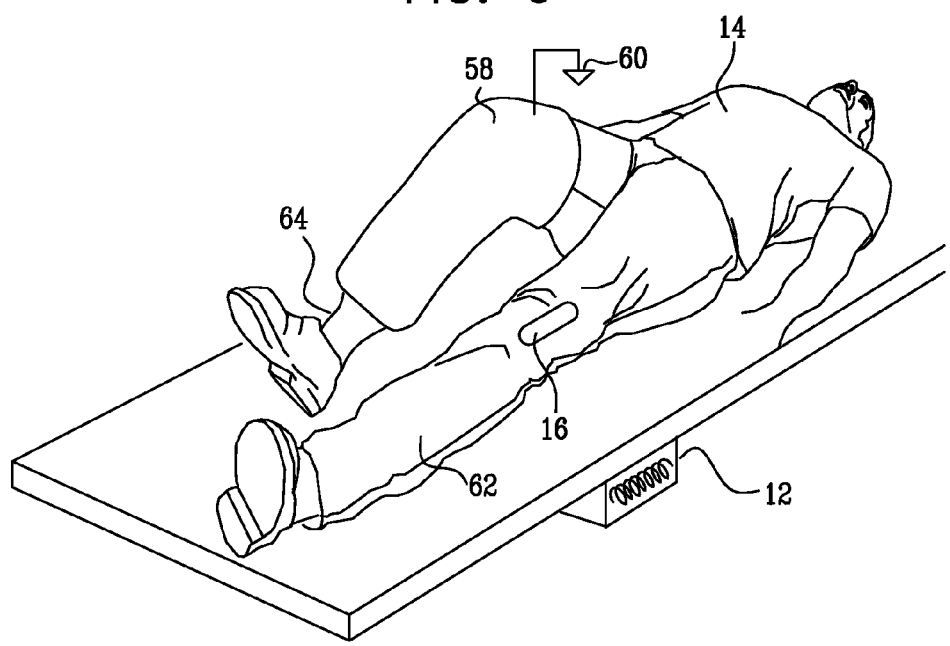
FIG. 6 is a pictorial illustration of a system for wirelessly powering a medical device that includes a protective shield, in accordance with an alternate embodiment of the invention.

Reference is now made to FIG. 6, which is a pictorial illustration of a system for wirelessly powering a medical device that includes a protective shield 58, in accordance with a disclosed embodiment of the invention. The shield 58, which comprises a material that blocks RF energy (e.g., aluminum foil, copper shields, brass, iron), is coupled to a ground 60 and placed between the power driving unit 12 and tissue of the subject 14 that need not be exposed to the field 26 (FIG. 1). In the example shown in FIG. 6, the medical device 16 has been implanted or inserted into a left leg 62 of the subject 14, and the shield 58 is configured to protect a right leg 64 from the field 26. Configurations for protecting other areas of the subject's body, and the physician (not shown) performing a medical procedure while powering the medical device 16, will be readily apparent to those skilled in the art. The shield 58 may be employed additionally or alternatively to the antenna 28 (FIG. 1).

The field created in the arrangement of FIG. 6 is not uniform. Nevertheless, addition of a reradiating antenna tends to decrease non-uniformities, as the effect of the field is relatively unchanged far from the antenna, and the field is reduced closer to the antenna.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

What is claimed is:

1. A method for wirelessly powering a medical device that is adapted to be disposed within a living subject, the method comprising the steps of:
   generating a radiofrequency energy field in a first direction from a first position outside said living subject, said radiofrequency energy field extending into said living subject to energize said medical device; and
   from a second position outside said living subject opposite to said first position from which said radiofrequency energy field is generated, reradiating in a second direction opposite to said first direction, at least a portion of said radiofrequency energy field such that said radiofrequency energy field is generally uniformly distributed between the first position and the second position.

2. The method according to claim 1, wherein said second position generally opposes said first position across said subject.

3. The method according to claim 1, wherein said device is a transponder having position sensors that obtain power from said field.

4. The method according to claim 1, wherein said step of reradiating said field is performed by disposing exactly one passive antenna at said second position.

5. The method according to claim 4, wherein said passive antenna comprises a single coil of wire.

6. The method according to claim 4, wherein said field has a frequency of 13.6 MHz and said passive antenna has a capacitance of about 100 pF.

7. The method according to claim 1, wherein said step of reradiating is performed by resonating said field at said second position.

8. The method according to claim 1, further comprising the step of shielding a portion of said subject from said field, said portion excluding said device.

9. The method according to claim 1, further comprising:
   positioning a reradiating element for said reradiation of said at least said portion of said radiofrequency energy field a specified distance from a radiofrequency driving unit for said generation of said radiofrequency energy field.

10. The method according to claim 1, further comprising:
    positioning a reradiating element for said reradiation of said at least said portion of said radiofrequency energy field between 1 meter and 1.5 meters from a radiofrequency driving unit for said generation of said radiofrequency energy field.

11. An apparatus for wirelessly powering a medical device that is adapted to be disposed within a living subject and that is energized by external radiofrequency energy, the apparatus comprising:
    a radiofrequency driving unit, adapted to be disposed at a first position outside said living subject, for generating a radiofrequency energy field in a first direction, to irradiate said medical device; and
    one or more reradiating elements adapted to be disposed in said radiofrequency energy field at a second position outside said living subject opposite to said first position at which said radiofrequency driving unit is disposed, to reradiate in a second direction opposite to said first direction, at least a portion of said radiofrequency energy field,
    wherein said one or more reradiating elements is configured to reradiate a portion of said radiofrequency energy field such that said radiofrequency energy field is generally uniformly distributed between the first position and the second position.

12. The apparatus according to claim 11, wherein said second position generally opposes said first position across said subject.

13. The apparatus according to claim 11, wherein said device is a transponder having position sensors that derive power from said field.

14. The apparatus according to claim 11, wherein said reradiating element is exactly one passive antenna.

15. The apparatus according to claim 14, wherein said passive antenna comprises a single coil of wire.

16. The apparatus according to claim 14, wherein said field has a frequency of 13.6 MHz and said passive antenna has a capacitance of about 100 pF.

17. The apparatus according to claim 14, wherein said passive antenna is resonant at a frequency of said field.

18. The apparatus according to claim 11, further comprising a shield that reduces exposure of a portion of said subject from radiant energy of said field.

19. The apparatus according to claim 11, wherein said reradiating element is position between 1 meter and 1.5 meters from said radiofrequency driving unit.

* * * * *